United States Patent [19]
Goldberg et al.

[11] Patent Number: 6,150,147
[45] Date of Patent: Nov. 21, 2000

[54] BIOLOGICAL ARRAY FABRICATION METHODS WITH REDUCTION OF STATIC CHARGE

[75] Inventors: Martin J. Goldberg, Saratoga; Mel Yamamoto, Fremont; Glenn H. McGall, Mountain View; Steven J. Woodman, San Jose; Eric Spence, Palo Alto; Lisa T. Kajisa, San Jose, all of Calif.

[73] Assignee: Affymetrix, Inc., Santa Clara, Calif.

[21] Appl. No.: 09/019,881

[22] Filed: Feb. 6, 1998

[51] Int. Cl.$^7$ .............. C12N 13/00; C12Q 1/68; C07H 21/00; H01G 3/00
[52] U.S. Cl. .............. 435/173.1; 435/6; 435/91.2; 536/25.3; 436/518; 436/527; 436/528; 361/213
[58] Field of Search .................. 435/173.1, 6, 91.2; 536/25.3; 436/518, 527, 528; 361/213

[56] References Cited

U.S. PATENT DOCUMENTS

| | | |
|---|---|---|
| 3,874,916 | 4/1975 | Livesay et al. . |
| 4,677,520 | 6/1987 | Price . |
| 4,689,715 | 8/1987 | Halleck et al. ............ 361/213 |
| 5,167,326 | 12/1992 | Murphy . |
| 5,384,261 | 1/1995 | Winkler et al. ............ 436/518 |
| 5,432,670 | 7/1995 | Batchelder et al. .......... 361/213 |
| 5,679,773 | 10/1997 | Holmes . |

FOREIGN PATENT DOCUMENTS

| | | |
|---|---|---|
| 0 695 941 | 5/1995 | European Pat. Off. . |
| 9-223673 | 8/1997 | Japan . |

OTHER PUBLICATIONS

Partial International Search Report dated Jun. 24, 1999 for PCT/US99/02515.

*Primary Examiner*—Jeffrey Fredman
*Attorney, Agent, or Firm*—Ellen M. Gonzales

[57] ABSTRACT

The present invention provides modified methods and apparatus for the preparation of arrays of material wherein each array includes a preselected collection of polymers, small molecules or inorganic materials associated with a surface of a substrate. The methods of the invention provide for modifications to general apparatus, flow cell geometries and solutions used in array fabrication.

49 Claims, 2 Drawing Sheets

BIOLOGICAL ARRAY FABRICATION METHODS WITH REDUCTION OF STATIC CHARGE

BACKGROUND OF THE INVENTION

Methods and apparatus for synthesizing a variety of different types of polymers are well known in the art. For example, the "Merrifield" method, described in Atherton et al., "Solid Phase Peptide Synthesis," IRL Press, 1989, which is incorporated herein by reference for all purposes, has been used to synthesize peptides on a solid support.

Methods have also been developed for producing large arrays of polymer sequences on solid substrates. These large "arrays" of polymer sequences have wide ranging applications and are of substantial importance to the pharmaceutical, biotechnology and medical industries. For example, the arrays may be used in screening large numbers of molecules for biological activity, e.g., receptor binding capability. Alternatively, arrays of nucleic acid probes can be used to identify mutations in known sequences. Of particular note, is the pioneering work described in U.S. Pat. No. 5,445,934 (Fodor et al.) and U.S. Pat. No. 5,510,270 (Fodor et al.) which disclose improved methods of molecular synthesis using light directed techniques.

SUMMARY OF THE INVENTION

The present invention provides modified methods and apparatus for the preparation of arrays of material wherein each array includes a preselected collection of polymers, small molecules or inorganic materials associated with a surface of a substrate. In one embodiment of the invention, a method of removing static charge during the fabrication of an array is described. The method of static charge removal may include, but is not limited to, the use of an ionizing fan. In another embodiment of the invention, optimized flow cell geometries are provided. In another embodiment of the invention, the introduction of phosphoramidite during array fabrication is provided. In another embodiment of the invention, a novel deprotection solution is provided.

DEFINITIONS

Figure 1:
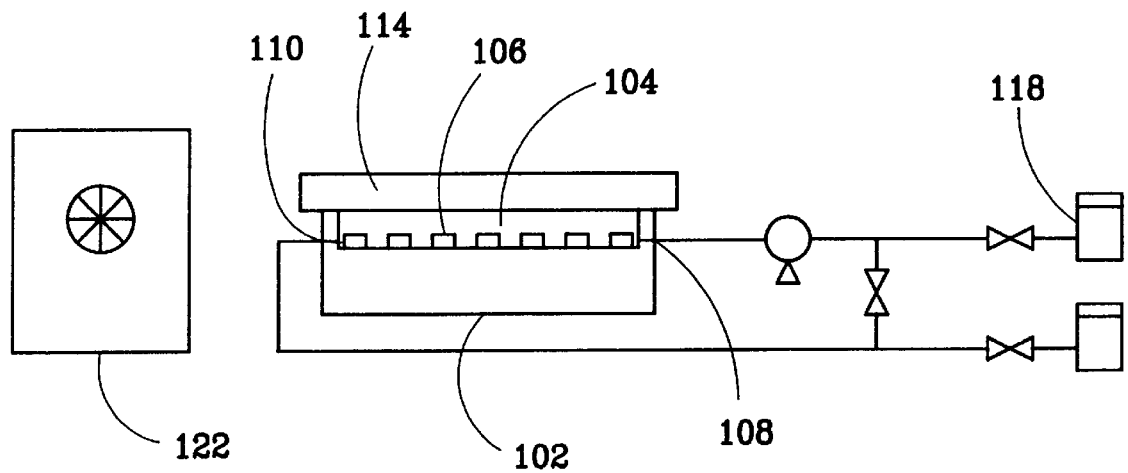
FIG. 1 schematically illustrates a reactor system for carrying out the combined photolysis chemistry steps of the present invention.

Array: An array is a preselected collection of different polymer sequences, small molecules or inorganic materials which are associated with a surface of a substrate. An array may include polymers of a given length having all possible monomer sequences made up of a specific basis set of monomers, or a specific subset of such an array. In other cases an array may be formed from inorganic materials (See Schultz et al PCT application WO 96/11878.)

Monomer: A member of the set of small molecules which can be joined together to form a polymer. The set of monomers includes but is not restricted to, for example, the set of common L-amino acids, the set of D-amino acids, the set of natural or synthetic amino acids, the set of nucleotides and the set of pentoses and hexoses. As used herein, monomer refers to any number of a basis set for synthesis of a polymer. For example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

Substrate: A material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

Protective Group: A material which is bound to a monomer unit and which may be selectively removed therefrom for exposure of a reactive group. A protective group generally prevents undesired reactions from taking place (such as coupling) until such time as the protective group is removed.

Reactive Group: Refers to a portion of a molecule which, under selected circumstances performs a desired coupling or cleavage reaction with another moiety. Such coupling may be via covalent or other types of bonds.

DESCRIPTION OF THE PRESENT INVENTION

Methods for synthesis of arrays of material have been previously described. For example, methods of synthesizing arrays of large numbers of polymer sequences, including oligonucleotide and peptides, on a single substrate have been described. See U.S. Pat. Nos. 5,143,854 and 5,384,261 and published PCT Application No. WO 92/10092, each of which is incorporated herein by reference in its entirety for all purposes. Methods for synthesizing arrays of inorganic materials have also been described. See published PCT Application No. WO 96/11878.

As described previously, the synthesis of materials on the surface of a substrate may be carried out using light directed methods as described in., e.g. U.S. Pat. Nos. 5,143,854 and 5,384,261 and Published PCT Application No. WO 92/10092, or mechanical synthesis methods as described in U.S. Pat. No. 5,384,261 and Published PCT Application No. WO 93/09668, each of which is incorporated herein by reference. In one embodiment, synthesis is carried out using light-directed synthesis methods. In particular, these light-directed or photolithographic synthesis methods involve a photolysis step and a chemistry step. Briefly, the substrate surface comprises functional groups on its surface.

These functional groups are protected by photo labile protecting groups ("photoprotected"). During the photolysis step, portions of the surface of the substrate are exposed to light or other activators to activate the functional groups within those portions, i.e., to remove photoprotecting groups. The substrate is then subjected to a chemistry step in which chemical monomers that are photoprotected at at least one functional group are then contacted with the surface of the substrate. These monomers bind to the activated portion of the substrate through an unprotected functional group.

Subsequent activation and coupling steps couple monomers to the other preselected regions, which may overlap with all or part of the first region. The activation and coupling sequence at each region on the substrate determines the sequence of the polymer synthesized thereon.

While light directed techniques are described herein by way of example, the inventions herein will have application to other technologies such as ink jet or flow cell synthesis methods see Winkler et al, U.S. Pat. No. 5,384,261, and through the use of applied electrical fields see Fodor et al, U.S. Pat. No. 5,143,854, or even placement of presynthesized materials on a support by the 25 above or other methods. See also co-pending U.S. Ser. No. 08/634,053, each of which is incorporated herein by reference in its entirety for all purposes.

The equipment involved in array fabrication can, particularly at certain times of the year, have a tendency to build up an inconsistent electrostatic charge, which can be either positive or negative. This electrostatic charge can, in some cases impact the consistency and quality of fabricated arrays. It is believed that this charge may be caused primarily by weather fluctuations, however, regardless of the cause, the removal or variation of the electrostatic charge can be beneficial to the fabrication process. Accordingly, the present invention provides, in one embodiment, for the removal of electrostatic charge from the fabrication process. This removal of electrostatic charge may be accomplished, for example, by the addition of ionizing fans, either large fans embedded in the ceiling above the equipment or small fans placed in areas which are recorded to have levels of electrostatic charge. In some particular cases, this electrostatic charge may be manipulated to enhance the performance of array fabrication, either in terms of a reduced length of time required for fabrication, or in an increased yield. In one particular example of fabrication of arrayed polymers through light-directed synthesis, the substrate preparation process combines the photolysis and chemistry steps in a single unit operation. The substrate wafer is mounted in a flow cell during both the photolysis and chemistry or monomer addition steps. In particular, the substrate is mounted in a reactor system that allows for the photolytic exposure of the synthesis surface of the substrate to activate the functional groups thereon. Solutions containing chemical monomers are then introduced into the reactor system and contacted with the synthesis surface, where the monomers can bind with the active functional groups on the substrate surface. The monomer containing solution is then removed from the reactor system, and another photolysis step is performed, exposing and activating different selected regions of the substrate surface. This process is repeated until the desired polymer arrays are created.

A schematic illustration of a device for carrying out the combined photolysis/chemistry step of the individual process is shown at FIG. 1. The figure shows a cross-sectional view of the reactor system 100. The device includes a flow cell which is made up of a body 102 having a cavity 104 disposed in one surface. The cavity generally includes fluid inlets 108 and outlets 110 for flowing fluid into and through the cavity. The cavity may optionally include ridges 106 on the back surface of the cavity to aid in mixing the fluids as they are pumped into and through the cavity. The substrate 112 is mounted over the cavity whereby the front surface of the substrate wafer 114 (the surface upon which the arrays are to be synthesized) is in fluid communication with the cavity. The device also includes a fluid delivery system in fluid connection with the fluid inlet 108 for delivering selected fluids into the cavity to contact the first surface of the substrate. The fluid delivery system typically delivers selected fluids, e.g. monomer containing solutions, index matching fluids, wash solutions, etc., from one or more reagent reservoirs 118, into the cavity via the fluid inlet 108. The delivery system typically includes a pump 116 and one or more valves to select from the various reagent reservoirs. Aspects of this invention are described in further detail in co-pending application Ser. No. 08/634,053 which is incorporated herein for all purposes. According to one preferred embodiment, an electrostatic charge removal device 122 is placed in contact or in proximity with the reactor system 100 for active removal of the charge. In one embodiment, this electrostatic removal device is a small portable electrostatic fan, in another embodiment it is a large fan embedded in the ceiling above the reactor system. In yet another embodiment, a charged static bar may be incorporated into a system wherein the ions from the bar are blown across the fabrication system by a nonelectrostatic fan. Other means of removing the electrostatic charge from the fabrication device will be apparent to one skilled in the art and this disclosure is not intended to be limited to the above named methods.

Figure 2:
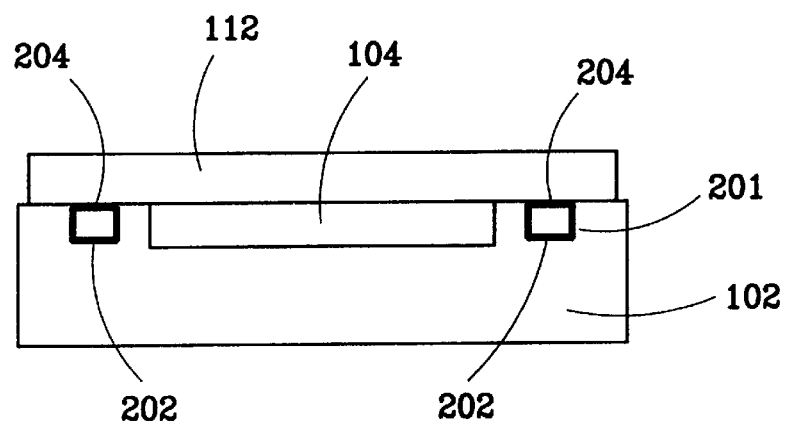
FIG. 2 depicts a cross-section of a flow cell design wherein shims are machined into the surface of the flow cell.

The present invention also provides design modifications to the flow cell. In one embodiment of the invention the flow cell body is designed in such as way as to form a contiguous body on which the substrate may fit while still allowing for the formation of a tight seal between the substrate and the flow cell body. It is believed that this design will prevent cracking of the substrate during the fabrication process. In one embodiment of the invention a shim often enclosing an o-ring is machined into the surface of the flow cell to form one contiguous surface. FIG. 2 depicts a cross-section of one embodiment of the flow cell design. A groove 201 is cut into the flow cell body 102 having a cavity 104. The shim 202, containing an o-ring 204, forms a tight seal between the body and the substrate 112 thereby creating a flat, contiguous surface where the substrate contacts the flow cell body.

It is often desirable to maintain the volume of the flow cell cavity as small as possible so as to more accurately control reaction parameters such as temperature or concentration of chemicals. However, flow cell cavities which are too small, as in a flow cell with a working depth of 0.010" or less for a flow cell measuring 5" in length and 5" in width, may lead to reduced yield by trapping bubbles from the reaction fluids in the cavity resulting in incomplete exposure of the substrate surface to the reaction fluid. It is important that the reagents in the flow cell cavity be allowed to mix completely. Flow cell cavities with an insufficient depth to length/width ratio may also interfere with complete mixing due to surface tension created by inadequate reaction volume size. Due to this factor, appropriate reaction cavity depth will vary with the width and length of the flow cell cavity. For a flow cell measuring 5"×5", preferred reaction cavity depths are 0.100" working depth to 0.005" working depth and more preferably 0.050" to 0.005", more preferably 0.032" to 0.010" with an 0.020" working depth being the most preferred.

In light directed synthesis, a monomer building block is introduced or contacted with the synthesis surface of the substrate following each photolysis step. The added monomer often includes a single active functional group, for example, in the case of oligonucleotide synthesis, a 3'-hydroxyl group. The remaining functional group that is involved in linking the monomer within the polymer sequence, e.g., the 5'-hydroxyl group of a nucleotide, is generally photoprotected. The monomers then bind to the reactive moieties on the surface of the substrate, activated during the preceding photolysis step, or at the termini of linker molecules of polymers being synthesized on the substrate.

The chemistry step often involves solid phase polymer synthesis methods that are well known in the art. For example, detailed descriptions of the procedures for solid phase synthesis of oligonucleotide by phosphoramidite, phosphite-triester, phosphotriester, and H-phosphonate chemistries are widely available. See Gait, ed. *Oligonucleotide Synthesis: A Practical Approach,* IRL Press, Washington D.C. (1984) which is incorporated herein by reference for all purposes.

In one embodiment of the invention, a solution containing a 3'-0-activated phosphoramidite nucleoside, photoprotected at the 5' hydroxyl is introduced into the flow cell for coupling to the photoactivated regions of the substrate. Typically the phosphoramidite nucleoside is present in the monomer solution at a concentration of from 1 mM to about 100 mM, more preferably at 10 mM to about 50 mM, more preferably at 15 mM to about 30 mM and most preferably at a concentration of about 20 mM.

Following overall synthesis of the desired polymers on the substrate wafers, permanent protecting groups, e.g., those which were not removed during each synthesis step, typically remain on nucleobases and the phosphate backbone of synthetic oligonucleotide. Removal of these protecting groups is usually accomplished with a concentrated solution of aqueous ammonium hydroxide. While this method is effective for the removal of the protecting groups, these conditions can also result in some amount of cleavage of the synthetic oligomers from the support (usually porous silica particles) by hydrolyzing an ester linkage between the oligo and a functionalized silane derivative that is bonded to the support. In arrays, it is desirable to preserve the linkage connecting the oligonucleotide to the substrate after the final deprotection step. For this reason, synthesis is carried out directly on the substrate which is derivatized with a hydroxylalkyl-trialkoxysilane (e.g., bis(hydroxyethyl) aminopropylsilane). However, these supports are not completely stable to the alkaline hydrolysis conditions used for deprotection. Depending upon the duration, substrates left in aqueous ammonia for protracted periods can suffer a loss of probes due to hydroxide ion attack on the silane bonded phase.

Co-pending application Ser. No. 08/634,053, which is incorporated herein for all purposes, describes final deprotection of the polymer sequence using anhydrous organic amines. In particular, primary and secondary alkylamines are used to effect final deprotection. The alkylamines may be used undiluted or in a solution of an organic solvent, e.g. ethanol, acetonitrile, or the like.

One embodiment of the present invention provides that the active ingredient in the solution be diluted in water. Preferred embodiments include, but are not limited to, Methylamine[MET]/$H_2O$, Ethylenediamine[EDA]/$H_2O$, Ethanolamine[ETA]/$H_2O$, and Ammonia Hydroxide/$H_2O$. Typically the solution of alkylamine will be at least about 40% alkylamine (v/v). Depending upon the protecting groups to be removed, the time required for complete deprotection in these solutions ranges from several minutes for "fast" base-protecting groups, e.g. PAC or DMF-protected A, C or G and Ibu-protected C, to from, for example, 4 to 20 hours for the standard protecting groups, e.g. benzoyl-protected A, C, or G and Ibu-protected G.

EXAMPLES

Temporary ionizing fans were first installed on or nearby areas where highly variable electrostatic charges were detected on the array fabrication equipment. Table 1 shows electrostatic field intensity measurements taken before ionization emitter fans were installed in the cleanroom pods. All measurements were taken with a Model 775PVS fieldmeter from Ion Systems, Inc.

TABLE 1

Measurement of static charge on apparatus (kV/inch)

| Location | Apparatus # A | B | C | Time of Measurement |
|---|---|---|---|---|
| Substrate wafer on load paddle before process (position 1) | +6.00 +8.00 | −4.00 −0.05 | −4.00 | Time 1 Time 1 + 5 hours |
| Substrate wafer on unload paddle after process (position 2) | +7.00 +10.0 | −4.00 −0.40 | −3.00 | Time 1 Time 1 + 5 hours |
| Flowcell door glass without substrate wafer before process (position 3) | −0.30 −0.40 | +0.10 −0.02 | | Time 1 Time 1 + 5 hours |
| Flowcell door glass without substrate wafer after process (position 3) | −0.70 +0.40 | +0.20 −0.02 | | Time 1 Time 1 + 5 hours |
| Flowcell insert (position 4) | +0.02 −0.02 | +0.01 +0.01 | −0.01 | Time 1 Time 1 + 5 hours |

Figure 3:
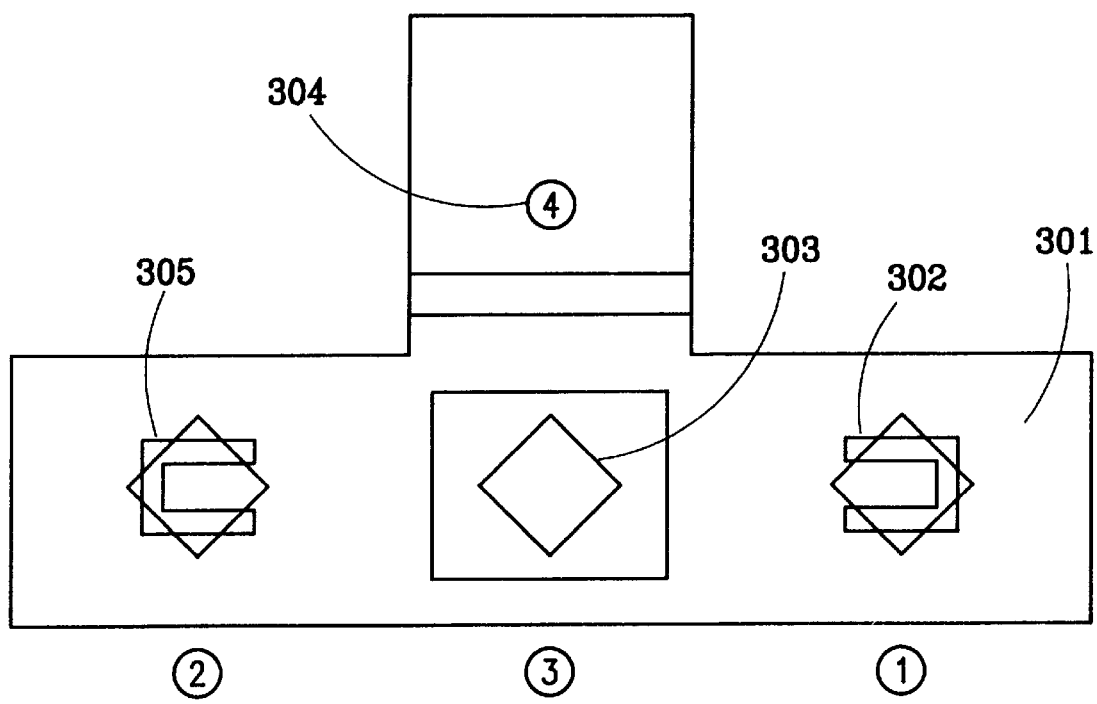
FIG. 3 schematically illustrates the locations of the electrostatic field measurements.

FIG. 3 depicts the location of electrostatic charge measurements. The apparatus 301 contains a load paddle 302, a flowcell 303, an unload paddle 305 and a flowcell insert 304. Measurements were taken in four locations, see FIG. 3, locations 1, 2, 3, and 4 where significant electrostatic intensities were previously observed. Reference measurements were also taken on a process development instrument located in another laboratory. Comparison of the numbers shows that the electrostatic charge can vary greatly both from one apparatus to another as well as on the same apparatus at different time points. The data in Table 2 show the intensities measured after ion emitter fans were installed on the instruments. Again the locations of the measurements refer to the locations in FIG. 3. Model 6440 and 6430 ion emitter fans products, also from Ion Systems, Inc. were used to neutralize the electrostatic fields.

TABLE 2

Electrostatic Measurements after Ion Fan Installation (kV/inch)

| Location | | Apparatus A | B | C |
|---|---|---|---|---|
| Wafer on load paddle before process (position 1) | Start charge level Ending charge level Time (seconds) | +1.33 0.00 8 | +1.35 −0.02 5 | +1.40 +0.02 5 |
| Wafer on unload paddle after process (position 2) | Start charge level Ending charge level Time (seconds) | +1.40 0.00 4 | +1.40 −0.01 5 | +1.44 +0.02 5 |
| Flowcell insert (position 4) | Start charge level Ending charge level Time (seconds) | +1.41 −0.02 4 | +1.40 −0.01 5 | +1.46 +0.02 5 |

Fieldmeter readings taken during the synthesis process on all three instruments show the ion emitter fans can effectively maintain static field levels at ±0.01 kV. Using a charge plate attached to the field meter, a 1–1.5 kV charge was applied and inserted into the ion flow to observe how quickly charges can be neutralized. All measurements show similar and consistent instrument performance. Steady state intensities level off at ±0.03 kV which are similar to background measurements.

It is believed that a deeper flow cell allows for better reagent mixing which results in greater synthesis uniformity. Table 3 summarizes the results of hybridization using 50 nM oligonucleotide target sequences under standard conditions of 30 minutes at 25 C. There is a noted improvement in both the average signal intensity and the corresponding chip coefficient of variation upon going to the 20 ml flow cell and using the 20 mM phosphoramidite concentration, coupled with a modular oligo synthesizer (MOS) cycle which features replenish coupling (see Replen. Couple in Table 3) where reagents are added, allowed to mix and then more of the same reagents are added before the cycle is completed to ensure complete reagent mixing during the cycle.

TABLE 3

Flow Cell Density and Phophoramidite Concentration

| Substrate | Flowcell Depth | [amid.] | Replen. Couple | Intensity | St. Dev. | % CV |
|---|---|---|---|---|---|---|
| A | 0.010" | 10 mM | No | 16987.0 | 823.2 | 4.8% |
| B | 0.010" | 10 | No | 15466.0 | 1355.6 | 8.8% |
| C | 0.020" | 10 | No | 18381.9 | 663.5 | 3.6% |
| D | 0.020" | 10 | No | 22089.0 | 1082.5 | 4.9% |
| E | 0.020" | 10 | Yes | 23266.8 | 442.2 | 1.9% |
| F | 0.020" | 20 | Yes | 25643.7 | 772.3 | 3.0% |

Wafers were synthesized under standard protocol conditions and then deprotected with methylamine [MET] (40% wt in $H_2O$) for 8 hours. The deprotected wafers were then diced, assembled and hybridized under standard protocol conditions. These wafers were analyzed and the results were compared with identically processed wafers deprotected with Ethylenediamine [EDA](50% wt in EtOH). The MET wafers demonstrated a 110% increase in foreground probe intensity, a 58% decrease in background probe intensity, and a 130%–400% increase in control probe intensity.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of fabricating an array comprising:
   fabricating materials on a surface of a substrate to form a biological array of materials; and
   removing static charge during said fabricating step.
2. The method of claim 1 wherein said fabrication step occurs in a reactor system.
3. The method of claim 2 wherein said reactor system comprises a flow cell.
4. The method of claim 1 wherein said materials are organic compounds.
5. The method of claim 1 wherein said materials are polymers.
6. The method of claim 4 wherein said polymers comprise nucleic acids.
7. The method of claim 1 wherein said removing static charge step is accomplished by an ionizing fan.
8. The method of claim 7 wherein said ionizing fan is a portable fan.
9. The method of claim 7 wherein said ionizing fan is permanently installed.
10. The method of claim 8 wherein said ionizing fan is installed in a ceiling.
11. A method of fabricating an array comprising:
    manipulating the static charge on a reactor;
    and fabricating materials using said reactor wherein said materials are organic compounds.
12. A method of fabricating an array comprising:
    fabricating materials on a surface of a substrate to form an array of organic materials, and;
    removing static charge during said fabrication step.
13. A method of fabricating an array comprising:
    fabricating materials on a surface of a substrate to form an array of materials wherein said materials are polymers comprising nucleic acids; and
    removing static charge during said fabrication step.
14. The method of claim 6 wherein said fan is placed in areas recorded to have levels of electrostatic charge.
15. The method of claim 6 wherein said fan is placed in close proximity to a location in which said fabricating step occurs.
16. The method of claim 1 wherein said removing static charge step is accomplished by an electrostatic fan.
17. The method of claim 1 wherein said removing static charge step is accomplished by a charged static bar.
18. The method of claim 17 wherein ions from said charged static bar are blown across said materials by a nonelectrostatic fan.
19. The method of claim 12 wherein said removing static charge step is accomplished by an ionizing fan.
20. The method of claim 19 wherein said ionizing fan is a portable fan.
21. The method of claim 19 wherein said ionizing fan is permanently installed.
22. The method of claim 21 wherein said ionizing fan is installed in a ceiling.
23. The method of claim 19 wherein said fan is placed in areas recorded to have levels of electrostatic charge.
24. The method of claim 19 wherein said fan is placed in close proximity to a location in which said fabricating step occurs.
25. The method of claim 12 wherein said removing static charge step is accomplished by an electrostatic fan.
26. The method of claim 12 wherein said removing static charge step is accomplished by a charged static bar.
27. The method of claim 26 wherein ions from said charged static bar are blown across said materials by a nonelectrostatic fan.
28. The method of claim 13 wherein said removing static charge step is accomplished by an ionizing fan.
29. The method of claim 28 wherein said ionizing fan is a portable fan.
30. The method of claim 28 wherein said ionizing fan is permanently installed.
31. The method of claim 30 wherein said ionizing fan is installed in a ceiling.
32. The method of claim 28 wherein said fan is placed in areas recorded to have levels of electrostatic charge.
33. The method of claim 28 wherein said fan is placed in close proximity to a location in which said fabricating step occurs.
34. The method of claim 13 wherein said removing static charge step is accomplished by an electrostatic fan.
35. The method of claim 13 wherein said removing static charge step is accomplished by a charged static bar.
36. The method of claim 35 wherein ions from said charged static bar are blown across said materials by a nonelectrostatic fan.

37. A method of fabricating an array comprising:

fabricating materials on a surface of a substrate to form an array of organic polymer materials; and removing static charge during said fabrication step.

38. The method of claim 37 wherein said removing static charge step is accomplished by an ionizing fan.

39. The method of claim 38 wherein said ionizing fan is a portable fan.

40. The method of claim 38 wherein said ionizing fan is permanently installed.

41. The method of claim 40 wherein said ionizing fan is installed in a ceiling.

42. The method of claim 38 wherein said fan is placed in areas recorded to have levels of electrostatic charge.

43. The method of claim 38 wherein said fan is placed in close proximity to a location in which said fabricating step occurs.

44. The method of claim 37 wherein said removing static charge step is accomplished by an electrostatic fan.

45. The method of claim 37 wherein said removing static charge step is accomplished by a charged static bar.

46. The method of claim 45 wherein ions from said charged static bar are blown across said materials by a nonelectrostatic fan.

47. A method of fabricating an array comprising:

reducing the static charge on a reactor and fabricating materials using said reactor where said materials are biological compounds.

48. A method of fabricating an array comprising:

reducing the static charge on a reactor and fabricating materials using said reactor where said materials are organic polymers.

49. A method of fabricating an array comprising:

reducing the static charge on a reactor and fabricating materials using said reactor where said materials are nucleic acids.

* * * * *